United States Patent
Michida

(10) Patent No.: US 9,333,498 B2
(45) Date of Patent: May 10, 2016

(54) ISOLATOR SYSTEM

(71) Applicant: PANASONIC HEALTHCARE HOLDINGS CO., LTD., Tokyo (JP)

(72) Inventor: Ayako Michida, Gunma (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 14/964,112

(22) Filed: Dec. 9, 2015

(65) Prior Publication Data

US 2016/0096171 A1    Apr. 7, 2016

Related U.S. Application Data

(63) Continuation of application No. PCT/JP2014/004358, filed on Aug. 25, 2014.

(30) Foreign Application Priority Data

Aug. 30, 2013 (JP) ................. 2013-179042

(51) Int. Cl.
| | | |
|---|---|---|
| *B01L 1/02* | (2006.01) | |
| *C12M 1/12* | (2006.01) | |
| *C12M 1/00* | (2006.01) | |
| *C12M 1/34* | (2006.01) | |
| *C12M 1/36* | (2006.01) | |

(52) U.S. Cl.
CPC ............... *B01L 1/025* (2013.01); *C12M 37/00* (2013.01); *C12M 41/14* (2013.01); *C12M 41/30* (2013.01); *C12M 41/48* (2013.01)

(58) Field of Classification Search
CPC ...... C12M 37/00; C12M 41/14; C12M 41/30; C12M 41/48; G01N 1/28; B01L 1/025
USPC ...................... 435/283.1; 422/292
See application file for complete search history.

(56) References Cited

U.S. PATENT DOCUMENTS

| | | | |
|---|---|---|---|
| 4,908,188 A | 3/1990 | Jefferis, III et al. | |
| 6,387,332 B1 | 5/2002 | Dickinson et al. | |
| 2011/0058986 A1* | 3/2011 | Yokoi ................... | A61L 2/0094 422/111 |
| 2012/0275967 A1 | 11/2012 | Yokoi et al. | |
| 2013/0336844 A1 | 12/2013 | Yokoi et al. | |

FOREIGN PATENT DOCUMENTS

| | | |
|---|---|---|
| JP | 62-502172 A | 8/1987 |
| JP | 11-206861 A | 8/1999 |
| JP | 11-332550 A | 12/1999 |
| JP | 2001-182346 A | 7/2001 |
| JP | 2008-011928 A | 1/2008 |
| JP | 2008-200126 A | 9/2008 |
| JP | 2009-225742 A | 10/2009 |
| JP | 2012-231918 A | 11/2012 |

OTHER PUBLICATIONS

International Search Report issued in International Application No. PCT/JP2014/004358 dated Sep. 30, 2014, with English translation.

* cited by examiner

*Primary Examiner* — Sean E Conley

(74) *Attorney, Agent, or Firm* — McDermott Will & Emery LLP

(57) ABSTRACT

An isolator system including: a body case; a sterilizing unit; an air conditioning unit; a display unit; a control unit; and a storage unit, the control unit being configured to, after startup, confirm whether a concentration of a sterilizing substance in a work area is equal to or less than a predetermined concentration, or not, and when the concentration of the sterilizing substance exceeds the predetermined concentration, store a high concentration flag in the storage unit, and thereafter, check an operation of the air conditioning unit, if there is no problem with the operation of the air conditioning unit, confirm whether the flag is stored, and when the flag is stored, operate the air conditioning unit for a predetermined time period, to lower the concentration of the sterilizing substance, and when the flag is not stored, end check of the operation of the air conditioning unit.

8 Claims, 15 Drawing Sheets

ISOLATOR SYSTEM

CROSS-REFERENCE TO RELATED APPLICATION

This is a continuation application of International Patent Application No. PCT/JP2014/004358 filed Aug. 25, 2014, which claims the benefit of priority to Japanese Patent Application No. 2013-179042 filed Aug. 30, 2013. The full contents of the International Patent Application are incorporated herein by reference.

BACKGROUND

1. Technical Field

The present disclosure relates to an isolator system used for experiments related to regenerative medicine and pharmaceutical production.

2. Description of the Related Art

Japanese Patent Application Laid-Open Publication No. 2009-225742 discloses an isolator configured to conduct work on tissue-derived biomaterials as target materials. The isolator includes: a working chamber; a reader configured to read information from a wireless tag that stores information associated with an operation target; and a work management unit configured to obtain information read with the reader, to manage work. Further, the isolator includes a monitor configured to display to a worker an operation menu for devices. Thus, work efficiency in the isolator is improved.

The present disclosure is to provide an isolator system capable of improving safety for workers.

SUMMARY

An isolator system according to the present disclosure, includes: a box-shaped body case including a work area, provided in an interior of the body case, in which work is conducted in a sterile environment, and an insertion portion, provided in a front surface of the body case, into which a worker's arm is inserted; a sterilizing unit configured to supply a sterilizing substance into the work area; an air conditioning unit configured to supply and/or discharge gas with respect to the work area; a display unit with which a worker inputs a signal; a control unit configured to be coupled to the sterilizing unit, the air conditioning unit, and the display unit; and a storage unit configured to store a signal from the control unit, the control unit being configured to, after startup, confirm whether a concentration of a sterilizing substance in the work area is equal to or less than a predetermined concentration, or not, and when the concentration of the sterilizing substance in the work area exceeds the predetermined concentration, store in the storage unit a high concentration flag indicative that the concentration of the sterilizing substance in the work area is high, and thereafter, check an operation of the air conditioning unit, and if there is no problem with the operation of the air conditioning unit, confirm whether the high concentration flag is stored in the storage unit, and when the high concentration flag is stored, operate the air conditioning unit for a predetermined time period, to lower the concentration of the sterilizing substance in the work area, and when the high concentration flag is not stored, end check of the operation of the air conditioning unit.

Other features of the present invention will become apparent from descriptions of the present specification and of the accompanying drawings.

BRIEF DESCRIPTION OF THE DRAWINGS

For more thorough understanding of the present invention and advantages thereof, the following description should be read in conjunction with the accompanying drawings, in which.

DETAILED DESCRIPTION

At least the following details will become apparent from descriptions of the present specification and of the accompanying drawings.

Hereinafter, embodiments will be described in detail with reference to drawings as necessary. However, more detailed description than necessity may be omitted. For example, the detailed descriptions of matters which have already well known and the repeated descriptions of substantially the same configurations may be omitted. This is because the following description is avoided from being redundant more than necessary, and facilitates the understanding by a person skilled in the art.

Note that the invertors provide the accompanying drawings and the following description to help a person skilled in the art fully understand the present disclosure, and are not intended to limit the subject matters described in the scope of claims thereby.

First Embodiment

An isolator system 100 will be described hereinafter as an example of an isolator system in a first embodiment with reference to FIGS. 1 to 14.

The isolator system 100 in the first embodiment is a device configured to perform, for example, work for cell culture, manipulation, observation, etc., in a sterile environment which has been sterilized. Sterilizing refers to an act of killing microorganisms, cells, etc., to bring a state closer to a sterile environment.

Note that, in the present embodiment, the Z-axis is an axis along a vertical direction in which the isolator system 100 is provided to stand, and it is assumed that a direction toward the upper side (upward) is +Z-direction and a direction toward the lower side (downward) is −Z-direction. The Y-axis is an axis along a direction substantially perpendicular to the front surface and the back surface of the isolator system 100, and it is assumed that a direction extending from the front surface, where at least an opening for conducting work within a work area is provided, to the back surface opposite to the front surface is −Y-direction, and a direction extending from the back surface to the front surface is +Y-direction. The X-axis is an axis along a direction substantially perpendicular to the side surfaces on the left and right sides when seen from the front, and it is assumed that a direction extending from the left side surface to the right side surface when seen from the front is +X-direction, and a direction extending from the right side surface to the left side surface is −X-direction.

[1-1. Configuration]

Figure 1:
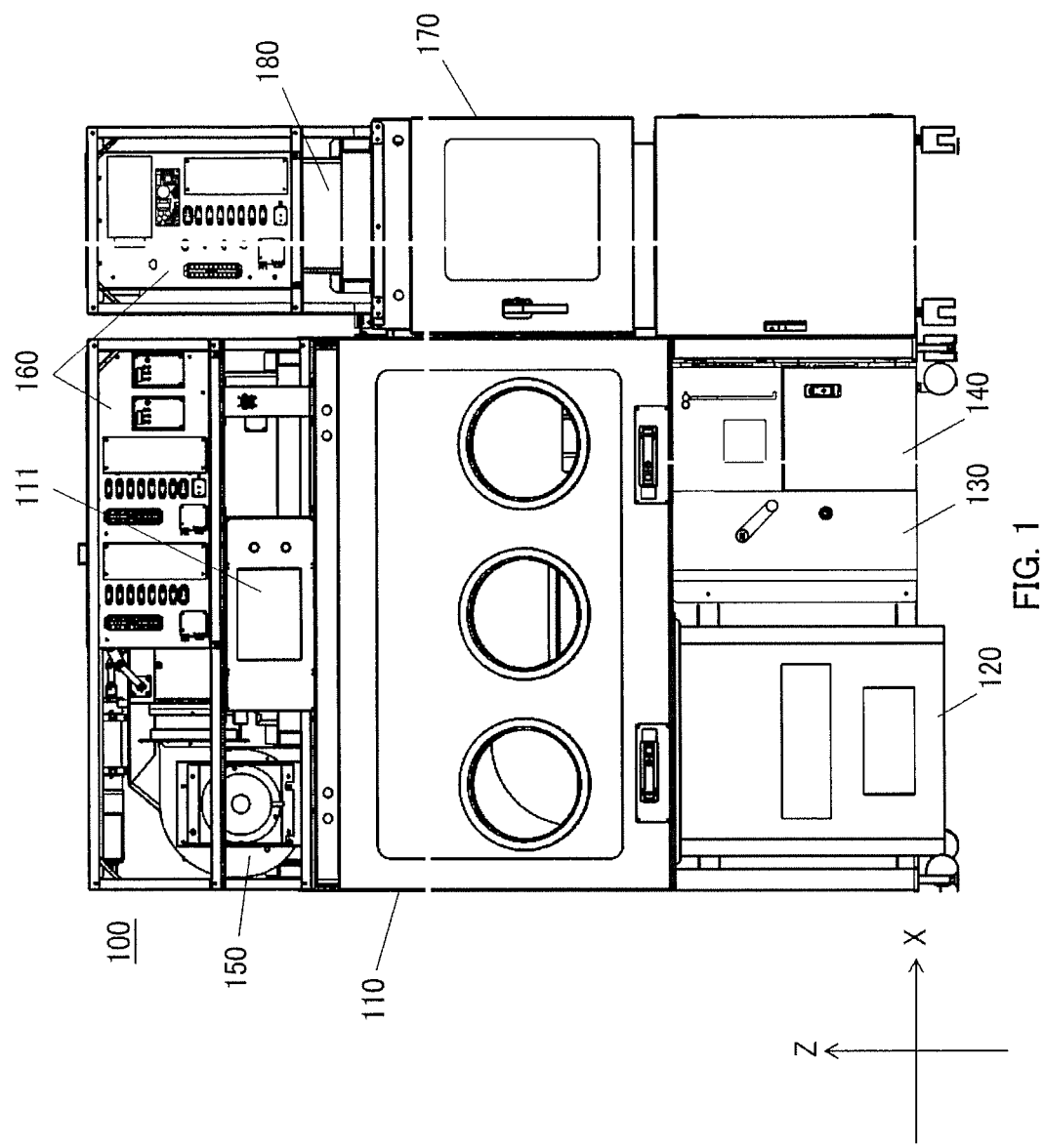
FIG. 1 is a front view illustrating an isolator system according to a first embodiment.
Figure 2:
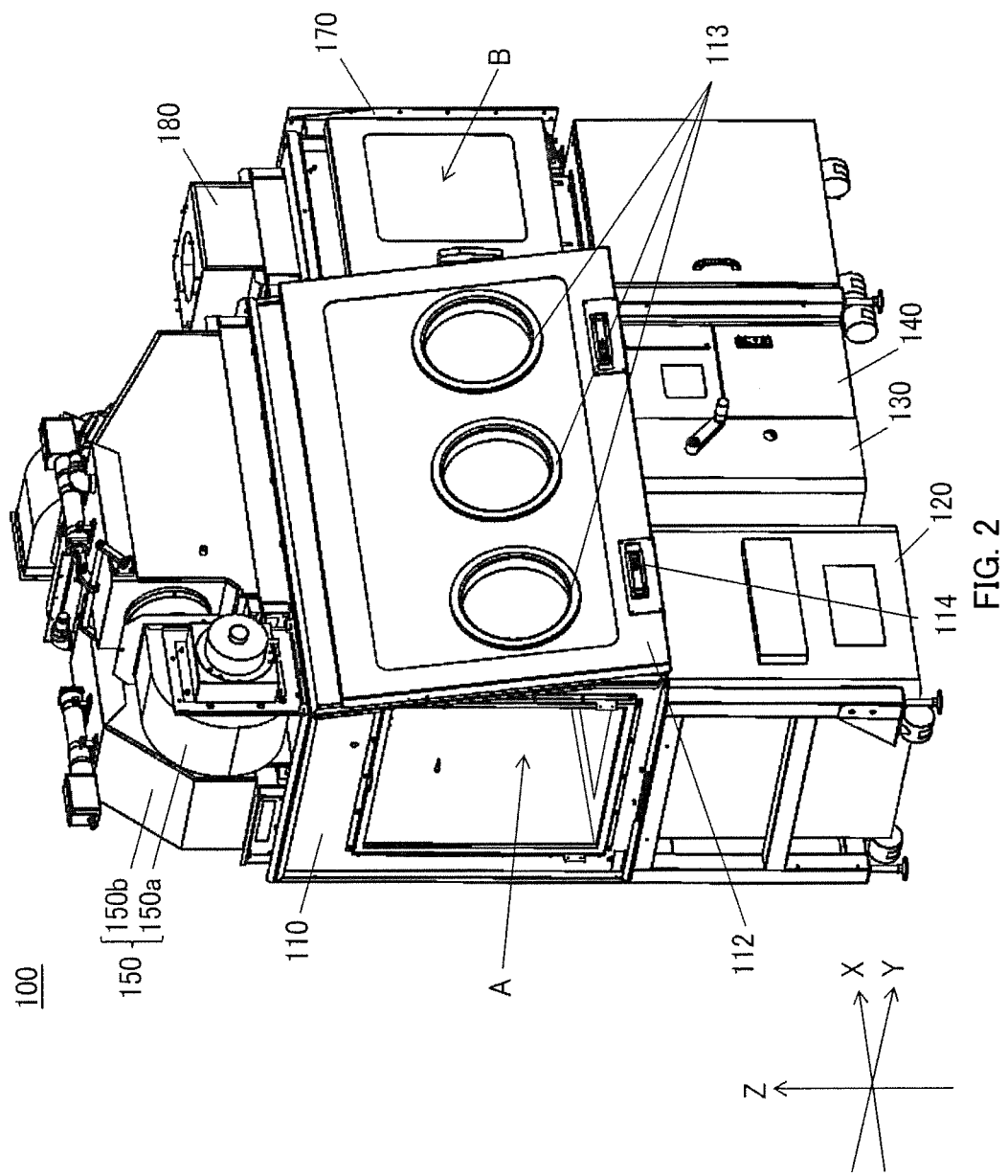
FIG. 2 is a perspective view illustrating the isolator system according to the first embodiment.

The overall configuration of the isolator system 100 will be described with reference to FIGS. 1 to 4. FIGS. 1 and 2 are a front view and a perspective view of the isolator system 100 according to the first embodiment, respectively.

Figure 4:
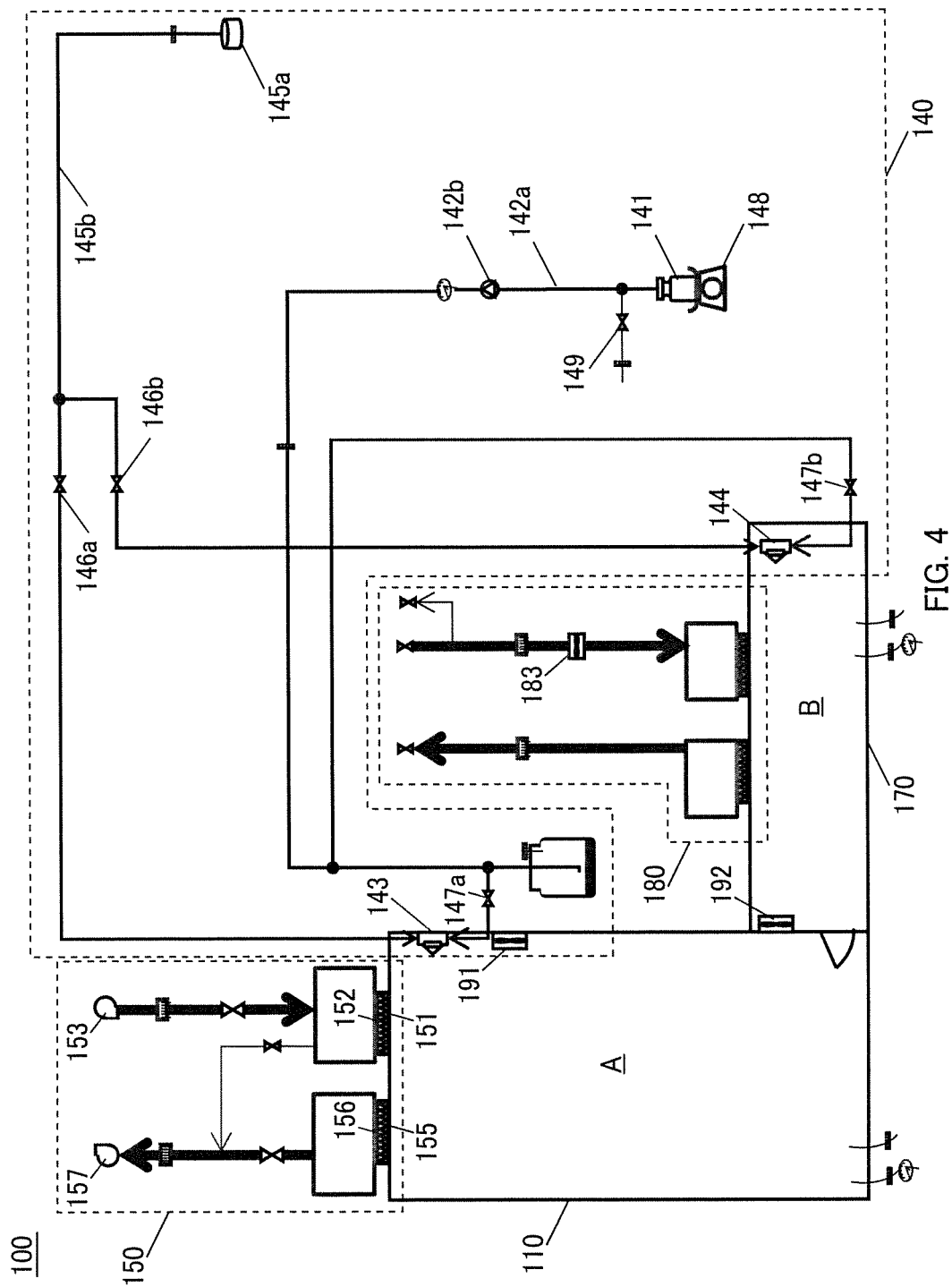
FIG. 4 is a schematic diagram illustrating a configuration of the isolator system according to the first embodiment.

As illustrated in FIG. 1, the isolator system 100 according to the first embodiment includes: a glove box 110; a centrifuge unit 120; an observation unit 130; a sterilizing unit 140; an air conditioning unit 150; a control unit 160; a pass box 170; an air conditioning unit 180; and diffusion fans 191, 192 (FIG. 4).

The glove box 110 includes a display 111 configured to display, at the upper front part thereof, an operation and/or a status of a device. The display 111 is configured to be coupled to the control unit 160 provided at the upper front part. A worker can input a signal with the display 111. As illustrated in FIG. 2, the glove box 110 has a substantially box-shaped work area A, formed therein, which configures a sterile environment isolated from the surroundings. The glove box 110 includes a front door 112 having at least an opening 113 provided in the front surface. The glove box 110 is formed to be partitioned with airtightness so as to restrain bacterial invasion from the outside. In the glove box 110, ducts for discharging the gas in the work area A are formed below a work platform, on which work is conducted, and on the backside of the work area A. The glove box 110 according to the present embodiment is configured with stainless steel plates, which are easily cleaned and sterilized.

The front door 112 is provided, in the front surface thereof, with the plurality of openings 113 for a worker's arms to be inserted thereinto, and gloves (not shown) are mounted to the plurality of openings 113, respectively. The front door 112 is openable and closable with respect to a hinge, serving as an axis, provided at an upper end portion. Thus, the front surface of the glove box 110 is openable and closable. Handles with locks 114, which are capable of locking the front door 112 as to opening/closing, are provided at the lower part of the front door 112. When opening the front door 112, a worker releases the locks of the handles with locks 114 and pulls the handles with locks 114 while holding them, thereby being able to open the front door 112. When closing the front door 112, a worker pushes down the front door 112, and then locks the handles with locks 114, thereby sealing the work area A.

The centrifuge unit 120 is provided below the glove box 110, and can be connected from the work area A. The centrifuge unit 120 includes, in the interior thereof, a centrifuge configured to centrifuge a sample to be worked on within the work area A.

The observation unit 130 is provided below the glove box 110, and can be connected from the work area A. The observation unit 130 includes, in the interior thereof, an observation device configured to observe a sample to be worked on within the work area A. Further, the observation unit 130 includes: an elevating mechanism capable of raising and lowering the observation device provided therewithin; and a handle, provided outside, with which the elevating mechanism is operated. A worker operates the elevating mechanism with the handle, thereby being able to lift the observation device into the work area A when the observation device is used, and accommodate the observation device in the observation unit 130 when the observation device is not used.

Figure 3:
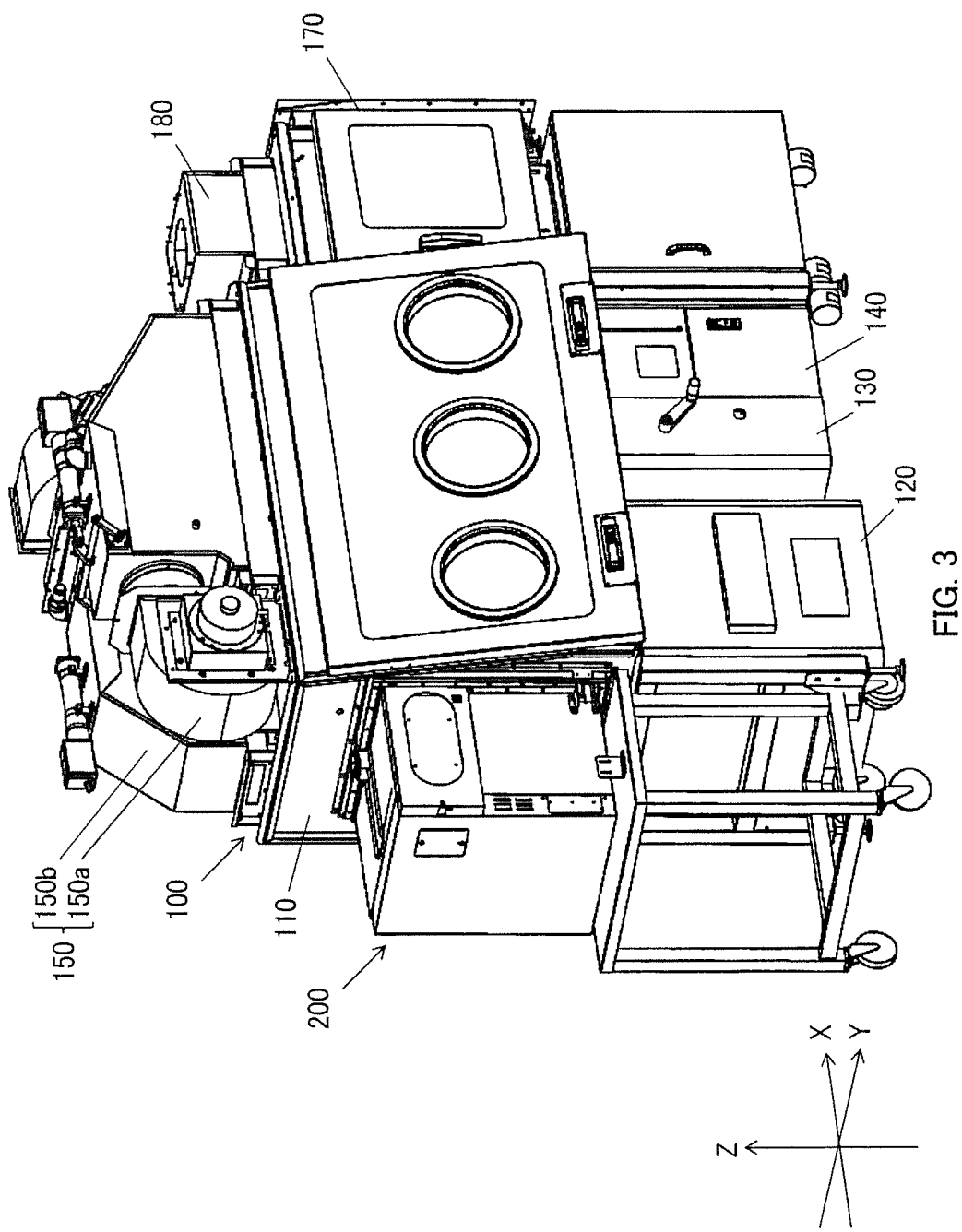
FIG. 3 is a perspective view illustrating the isolator system according to the first embodiment when an incubator is mounted thereto.

FIG. 3 is a perspective view illustrating the isolator system 100 according to the first embodiment when an incubator 200 is mounted thereto. As illustrated in FIG. 3, in the isolator system 100, the incubator 200 is mounted on the side surface opposite to the side surface of the glove box 110 to which the pass box 170 is mounted. The incubator 200 includes a storage chamber (not shown) in the interior thereof. The storage chamber is a chamber in which a culture is stored, and is partitioned, as a space for restraining bacterial invasion from the outside, by a rectangular parallelepiped-shaped box body, for example. The storage chamber is partitioned with, for example, stainless steel plates. The incubator 200 is demountably configured with respect to the isolator system 100. As a result, culture can be controlled in each incubator 200. For example, a dedicated incubator 200 is used for each donor, thereby being able to restrain occurrence of failures such as mix-ups of cultures.

The sterilizing unit 140 is provided below the glove box 110 so as to supply a sterilizing substance to sterilize the work area A in the glove box 110. FIG. 4 is a schematic diagram illustrating a configuration of the isolator system 100 according to the first embodiment. As illustrated in FIG. 4, the sterilizing unit 140 includes: a sterilizing liquid bottle 141; an electronic balance 148 configured to measure the weight of the sterilizing liquid bottle 141; and a water suction tube 142a and a peristaltic pump 142b for suctioning the sterilizing liquid from the sterilizing liquid bottle 141 to supply it to the nozzle 143 or the nozzle 144. The sterilizing unit 140 further includes: the nozzle 143 provided within the glove box 110; and the nozzle 144 provided within the pass box 170. The sterilizing unit 140 further includes a compressor 145a and an air supply tube 145b for supplying air to the nozzle 143 or the nozzle 144. The sterilizing unit 140 also includes: an air supply valve 149 for introducing the air into the water suction tube 142a. The air supply valve 149 is provided between the tip of the water suction tube 142a inserted into the sterilizing liquid bottle 141 and the peristaltic pump 142b. A switching valve 146a and a switching valve 146b are configured to be opened/closed, to control the flow of the air into the nozzle 143 or the nozzle 144. A switching valve 147a and a switching valve 147b are configured to be opened/closed, to control the flow of the sterilizing liquid into the nozzle 143 or the nozzle 144.

For example, a hydrogen peroxide solution is used as the sterilizing liquid. The sterilizing liquid is stored in the sterilizing liquid bottle 141, and the sterilizing liquid bottle 141 is placed on a measurement means such as the electronic balance 148. The electronic balance 148 is configured to measure the weight of the sterilizing liquid bottle 141 and the sterilizing liquid, and its signal is inputted to the control unit 160. The sterilizing liquid stored in the sterilizing liquid bottle 141 is to be supplied by a liquid delivery means, such as the peristaltic pump 142b, through the water suction tube 142a to the nozzle 143 or the nozzle 144. The hydrogen peroxide solution in the sterilizing liquid bottle 141 is supplied in a gradual manner by the peristaltic pump 142b to the nozzle 143 or the nozzle 144. The peristaltic pump 142b is provided to the water suction tube 142a, and a filter configured to remove foreign substances is provided on the downstream side with respect to the peristaltic pump 142b. A pressure sensor configured to detect the pressure within the water suction tube 142a is provided between the filter and the peristaltic pump 142b. With the pressure sensor, it is possible to monitor the clogging of the filter or detect abnormality such as bending of the water suction tube 142a. Since signals from the electronic balance 148 and the pressure sensor are inputted to the control unit 160, the control unit 160 can control driving of the peristaltic pump 142b and opening/closing of the air supply valve 149. Further, one end of the air supply tube 145b is mounted to the compressor 145a, and the other end thereof is mounted to the nozzle 143 or the nozzle 144. Thereby, the compressor 145a can supply air through the air supply tube 145b to the nozzle 143 or the nozzle 144.

As illustrated in FIG. 3, the air conditioning unit 150 is provided above the glove box 110 and is configured to control supply/discharge with respect to the work area A. The air conditioning unit 150 includes an air supply unit 150a and a discharge unit 150b. As illustrated in FIG. 4, the air conditioning unit 150 includes an air supply inlet 151 and a discharge outlet 155 provided on an upper surface plate in the glove box 110. The air is supplied into the glove box 110 from the air supply inlet 151, and is discharged from the discharge outlet 155. In the glove box 110, in order to secure a sterile environment in the interior thereof, a particulate trap filter of an HEPA filter 152 is mounted to the air supply inlet 151, and the air is supplied through the particulate trap filter into the glove box 110. An HEPA filter 156 is also mounted to the discharge outlet 155, and the gas within the glove box 110 is discharged through the HEPA filter 156 from the interior of the glove box 110. In the glove box 110, a sterilizing substance such as hydrogen peroxide is sprayed thereinto, and thereby sterilization processing of sterilizing the interior of the glove box 110 is performed.

Figure 5:
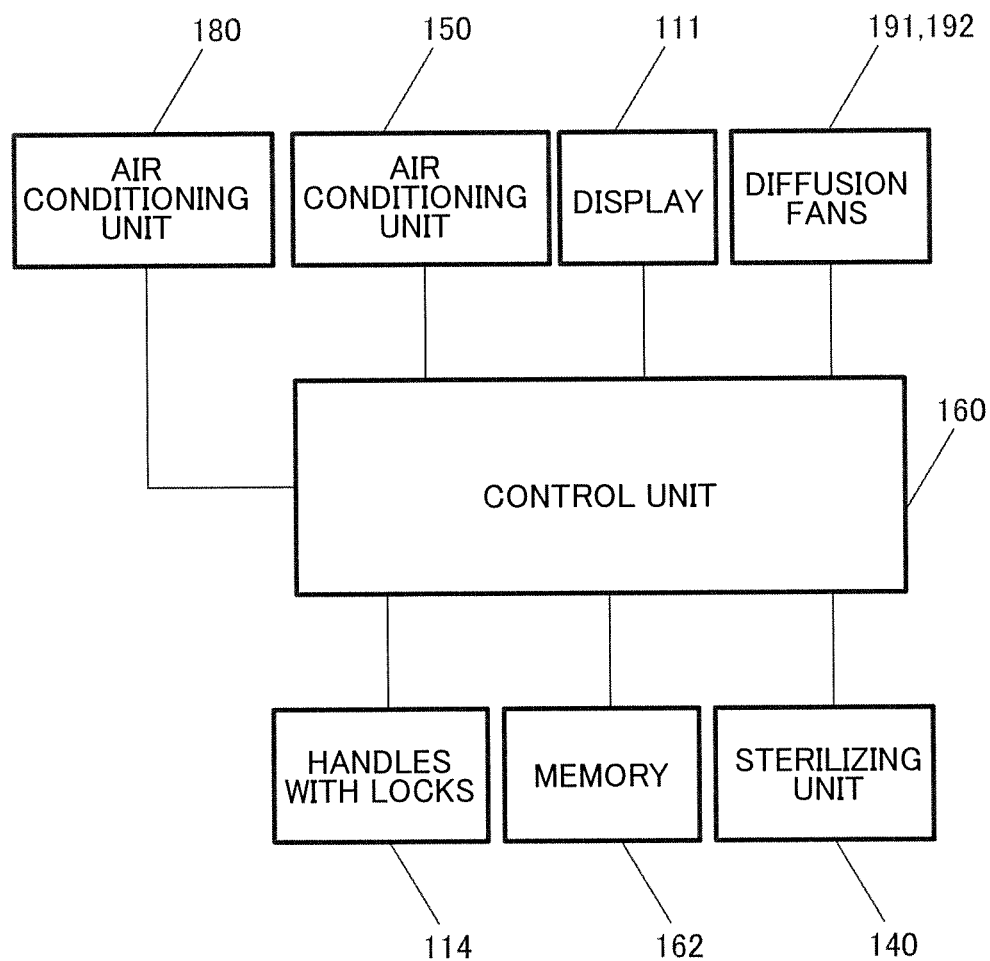
FIG. 5 is a block diagram illustrating a configuration of the isolator system according to the first embodiment.

FIG. 5 is a block diagram illustrating a configuration of the isolator system according to the first embodiment. As illustrated in FIG. 5, the control unit 160 is configured to be coupled to a memory 162, the display 111, the handles with locks 114, the sterilizing unit 140, the air conditioning unit 150, the air conditioning unit 180 (FIG. 3) and the diffusion fans 191, 192 (FIG. 4). The memory 162 is configured to store a signal transmitted from the control unit 160. The display 111 is configured to display the signal transmitted from the control unit 160. The handles with locks 114 are configured to lock the front door 112 as to opening/closing of the front door 112, or release the locks, in response to the signal transmitted from the control unit 160. The signal is outputted to components of the sterilizing unit 140, in response to an input from the electronic balance 148, etc. The sterilizing unit 140 is configured to operate the components in response to the signal transmitted from the control unit 160 to spray a sterilizing mist. The air conditioning unit 150 and the air conditioning unit 180 are configured to control an air supply blower 153, a discharge blower 157, and an air supply blower 183, based on the signal transmitted from the control unit 160, to supply outside air (gas) and discharge inside air. The diffusion fans 191, 192 are controlled based on the signal transmitted from the control unit 160. The control unit 160 is configured to perform a pre-operation check for checking devices and a sterilization process for sterilizing the interior of the glove box 110. The sterilization process includes a spray process, an exposure process, and a detoxification process. The spray process is a process of spraying the sterilizing mist (sterilizing substance) in the interior of the glove box 110 to sterilize it. The exposure process is a process of diffusing the sprayed sterilizing mist over the entire interior of the glove box 110 to sterilize it. The detoxification process is a process of supplying the air to the interior of the glove box 110 while discharging the gas in the glove box 110, to exchange the gas in the glove box 110, thereby reducing the concentration of the sterilizing substance in the interior of the work area A.

As illustrated in FIG. 2, the pass box 170 is provided on the side surface of the glove box 110 so that a worker puts a work item into the work area A from the outside. In the interior of the pass box 170, a transport space B for temporarily storing the work item is formed. The transport space B has hermeticity against the surrounding environment. Before the work item is put into the work area A from the outside, the work item is sterilized within the transport space B. In the side surface of the pass box 170, an opening for moving the work item is provided, and the glove box 110 and the pass box 170 are fixed so that the opening in the side surface of the pass box 170 is opposed to an opening provided in the side surface of the glove box 110. Thus, the work area A and the transport space B communicate with each other with hermeticity being maintained. A door that is openable and closable is mounted to the opening of the pass box 170. The door can separate the transport space B and the work area A with hermeticity being maintained. The air conditioning unit 180 is provided above the pass box 170 and is configured to control air conditioning within the transport space B.

Further, the isolator system 100 according to the present embodiment includes the diffusion fans 191, 192. The diffusion fan 191 is provided in the glove box 110, and the diffusion fan 192 is provided in the pass box 170. The diffusion fan 191 is configured to diffuse the gas in the interior of the work area A, and the diffusion fan 192 is configured to diffuse the gas in the interior of the transport space.

[1-2. Operation]

An operation of the isolator system 100 configured as above will hereinafter be described.

Figure 6:
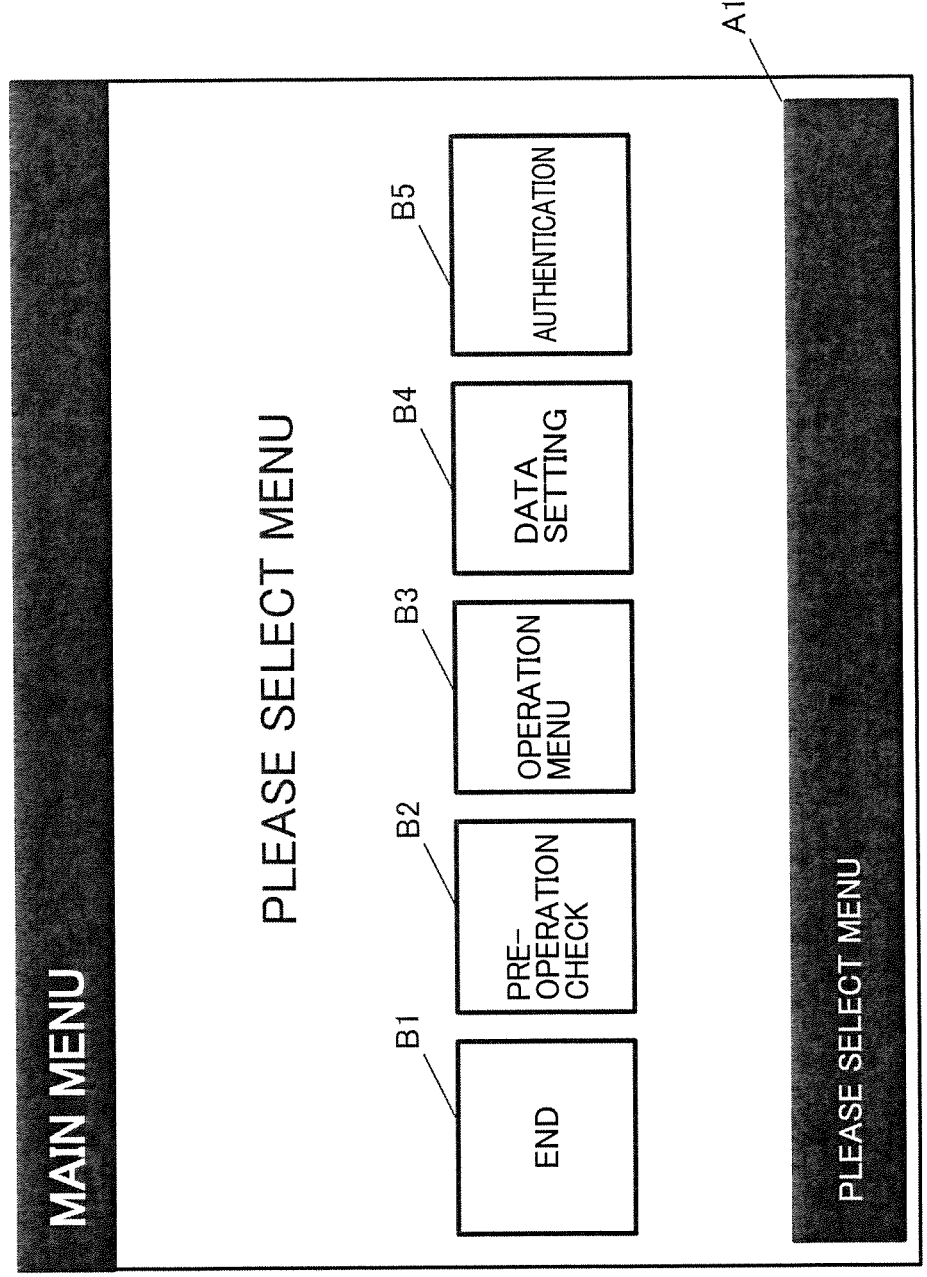
FIG. 6 is a diagram illustrating a main menu screen after startup of the isolator system according to the first embodiment.

FIG. 6 is a diagram illustrating a main menu screen after startup of the isolator system according to the first embodiment.

When the isolator system 100 is started, the control unit 160, firstly, displays a main menu screen illustrated in FIG. 6 on the display 111. A worker selects a menu to be operated from the main menu screen, to operate the isolator system 100. The main menu screen displays an [END] button B1 for ending the operation of the isolator system 100, a [PRE-OPERATION CHECK] button B2 for checking the device, an [OPERATION MENU] button B3 for operating the sterilization process, etc., a [DATA SETTING] button B4 for setting various data, and an [AUTHENTICATION] button B5 for performing authentication of a worker.

Figure 7:
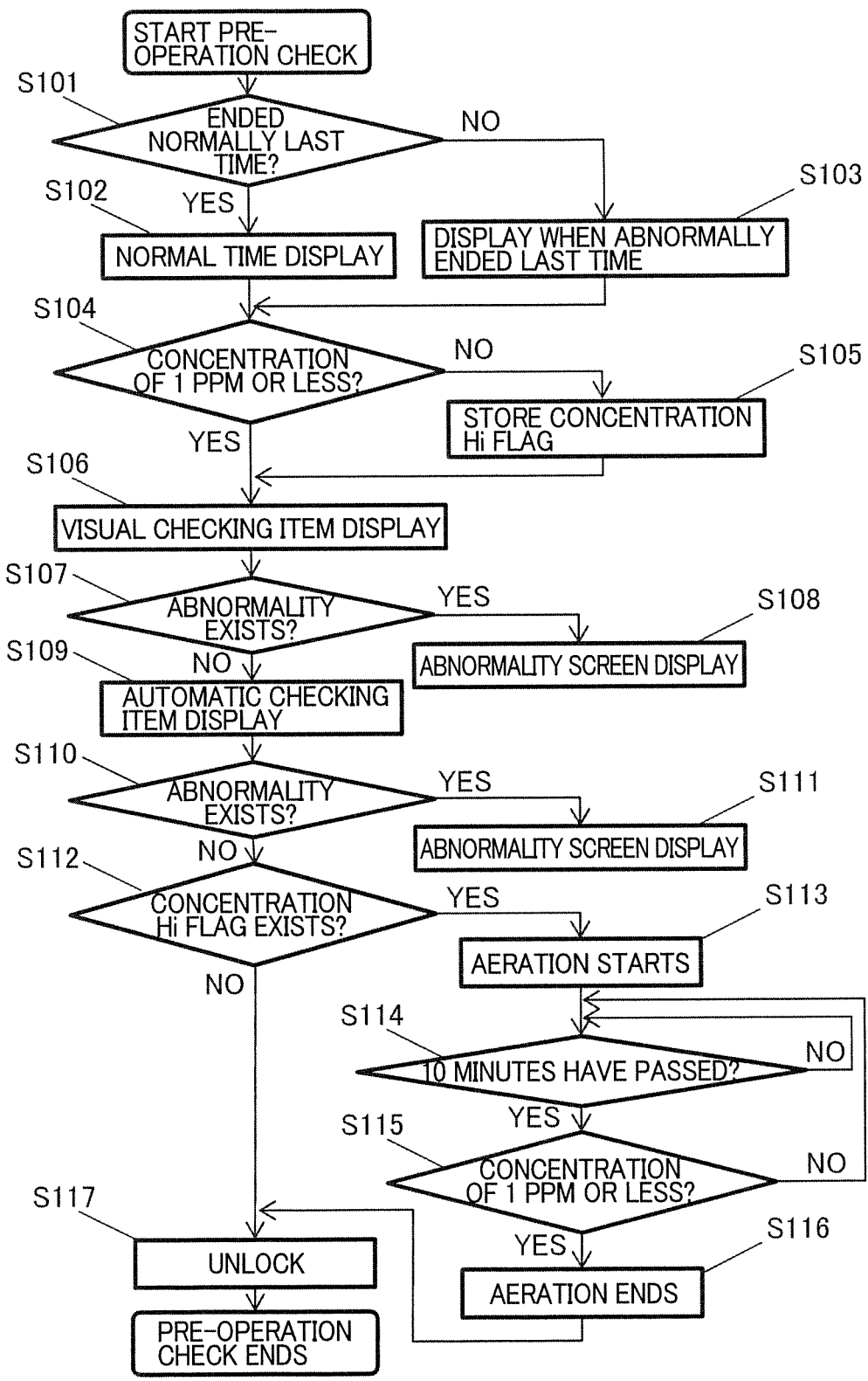
FIG. 7 is a flow chart illustrating a pre-operation check of the isolator system according to the first embodiment.

Here, the pre-operation check for checking devices will be described in detail. FIG. 7 is a flowchart illustrating the pre-operation check of the isolator system according to the first embodiment.

As illustrated in the flow chart of FIG. 7, when the pre-operation check is selected, the control unit 160, firstly, confirms whether the operation normally ended when the previous operation ended (S101). The normal end of the operation indicates that a worker instructs termination of the operation and thereby the operation ends. On the other hand, the abnormal end of the operation indicates that electric power supply to the device is interrupted, for example, due to power failure caused by lightning strike or the like, resulting in the device being forcibly shut down. Note that, in the isolator system 100 according to the present embodiment, the front door 112 is locked with the handles with locks 114 when power supply is OFF. Thus, when the isolator system 100 is started, the handles with locks 114 are in a state of being locked.

Figure 8:
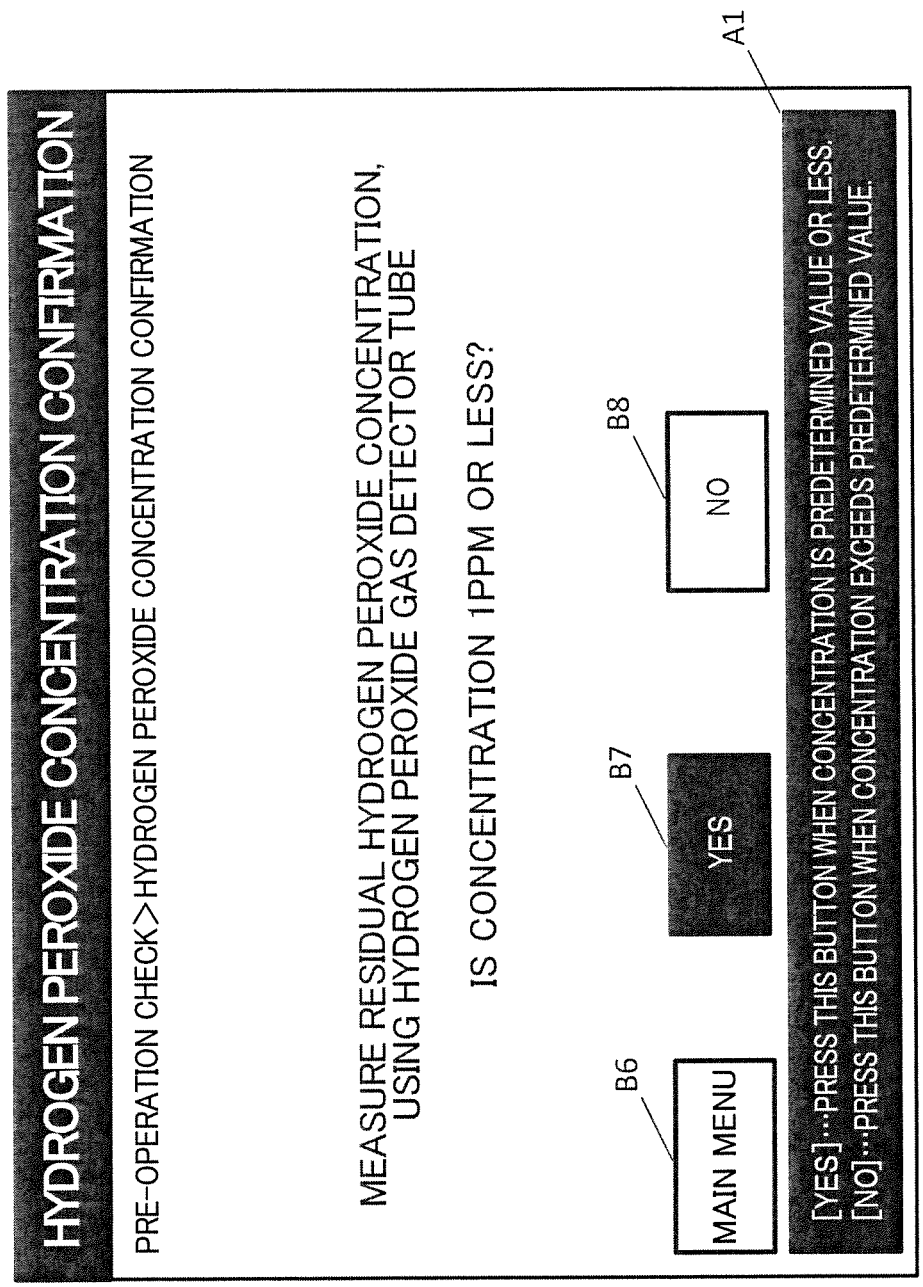
FIG. 8 is a diagram illustrating a hydrogen-peroxide concentration confirmation screen at normal time when the pre-operation check of the isolator system according to the first embodiment is performed.

When the previous operation ended normally, the control unit 160 displays a screen illustrated in FIG. 8 on the display 111 (S102). FIG. 8 is a diagram illustrating a normal hydrogen-peroxide concentration confirmation screen at normal time when the pre-operation check of the isolator system 100 according to the first embodiment is performed. As illustrated in FIG. 8, the normal hydrogen-peroxide concentration confirmation screen displays: an instruction for measuring the concentration of hydrogen peroxide to a worker; a question as to whether the concentration of hydrogen peroxide is equal to or less than the predetermined concentration or not; and a [YES] button B7 and a [NO] button B8 (concentration confirmation input part) for inputting a reply to the question. The screen displays also a [MAIN MENU] button 56 for returning to the main menu screen and an operating instruction space A1 for providing an instruction of an operation method to a worker, on the same screen.

Figure 9:
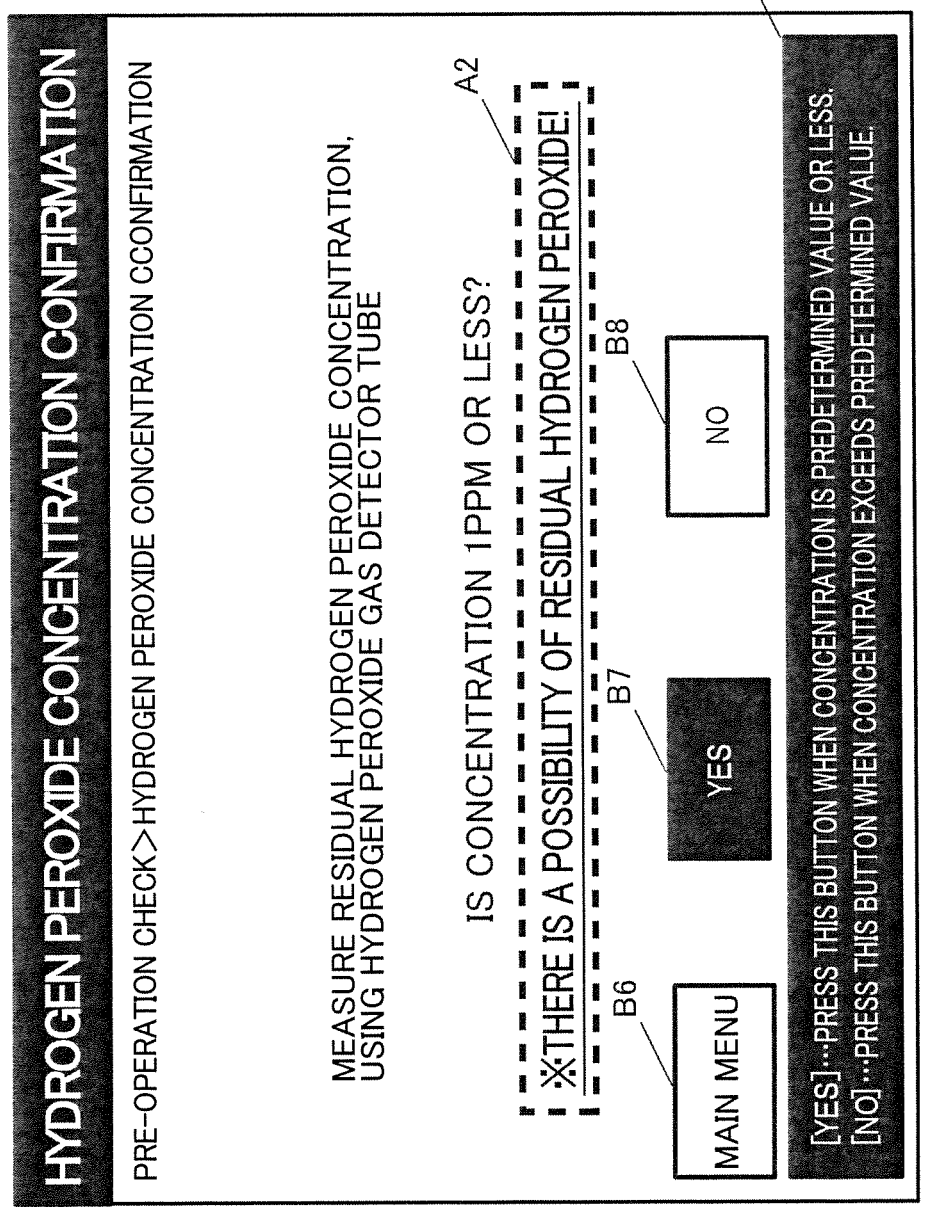
FIG. 9 is a diagram illustrating a hydrogen-peroxide concentration confirmation screen indicative that the isolator system according to the first embodiment abnormally ended last time, when the pre-operation check of the isolator system is performed.

On the other hand, when the previous operation did not normally end, that is, when the operation abnormally ended last time, the control unit 160 displays the screen illustrated in FIG. 9 on the display 111 (S103). FIG. 9 is a diagram illustrating a hydrogen-peroxide concentration confirmation screen indicative that the isolator system 100 according to the first embodiment abnormally ended last time, when the pre-operation check of the isolator system is performed. As illustrated in FIG. 9, on the hydrogen-peroxide concentration confirmation screen when the device abnormally ended last time, the screen at normal time illustrated in FIG. 8 is displayed with a precaution space A2, including a precaution for a worker, being added. This is to call a worker's attention by displaying the precaution space A2, since there is a possibility that the concentration of hydrogen peroxide is high in the glove box 110 when the operation is abnormally ended, for example, due to a power failure during the sterilization process or the like.

A worker measures the concentration of hydrogen peroxide remaining in the work area A, using a hydrogen peroxide gas detector tube, in response to the question illustrated in FIGS. 8, 9, and inputs the results with the display 111.

Subsequently, when the worker selects the [NO] button B8 on the hydrogen peroxide confirmation screen, the control unit 160 stores, in the memory 162, a "concentration Hi flag" indicative that the concentration of hydrogen peroxide in the glove box 110 is high, and thereafter displays a device check screen illustrated in FIG. 10 on the display 111 (S104, S105, S106). On the other hand, when the worker selects the [YES] button B7, the control unit 160 displays the device check screen illustrated in FIG. 10 on the display 111, without storing the "concentration Hi flag" in the memory 162 (S104, S106). Although not illustrated in FIG. 7, in the present embodiment, when the worker selects the [YES] button B7, the control unit 160 releases the locks of the handles with locks 114, to enable opening/closing of the front door 112. On the other hand, when the worker selects the [NO] button B8, the control unit 160 does not release the locks of the handles with locks 114, with the front door 112 remaining locked as to opening/closing.

Figure 10:
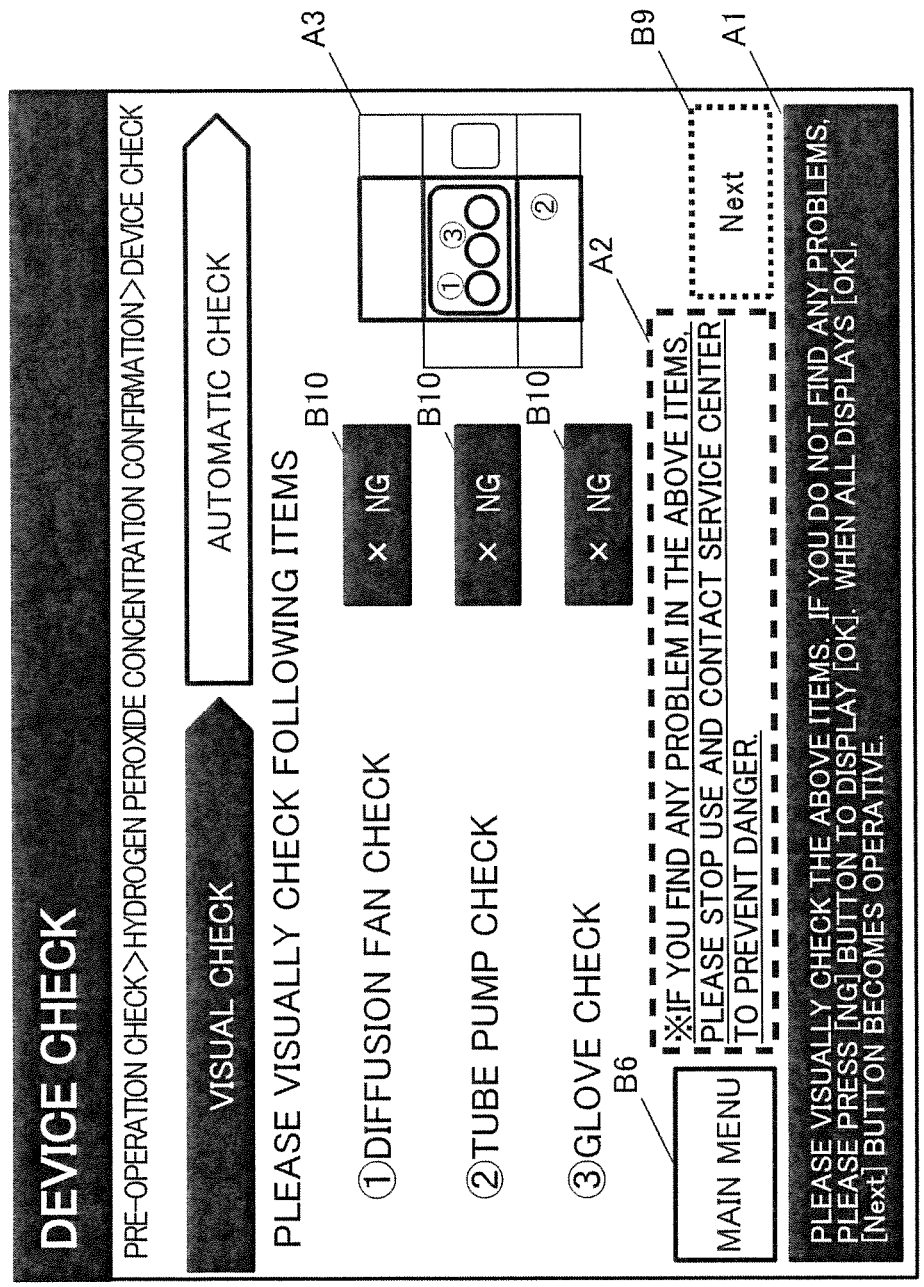
FIG. 10 is a diagram illustrating a device check screen when a visual check in the pre-operation check of the isolator system according to the first embodiment is performed.
Figure 11:
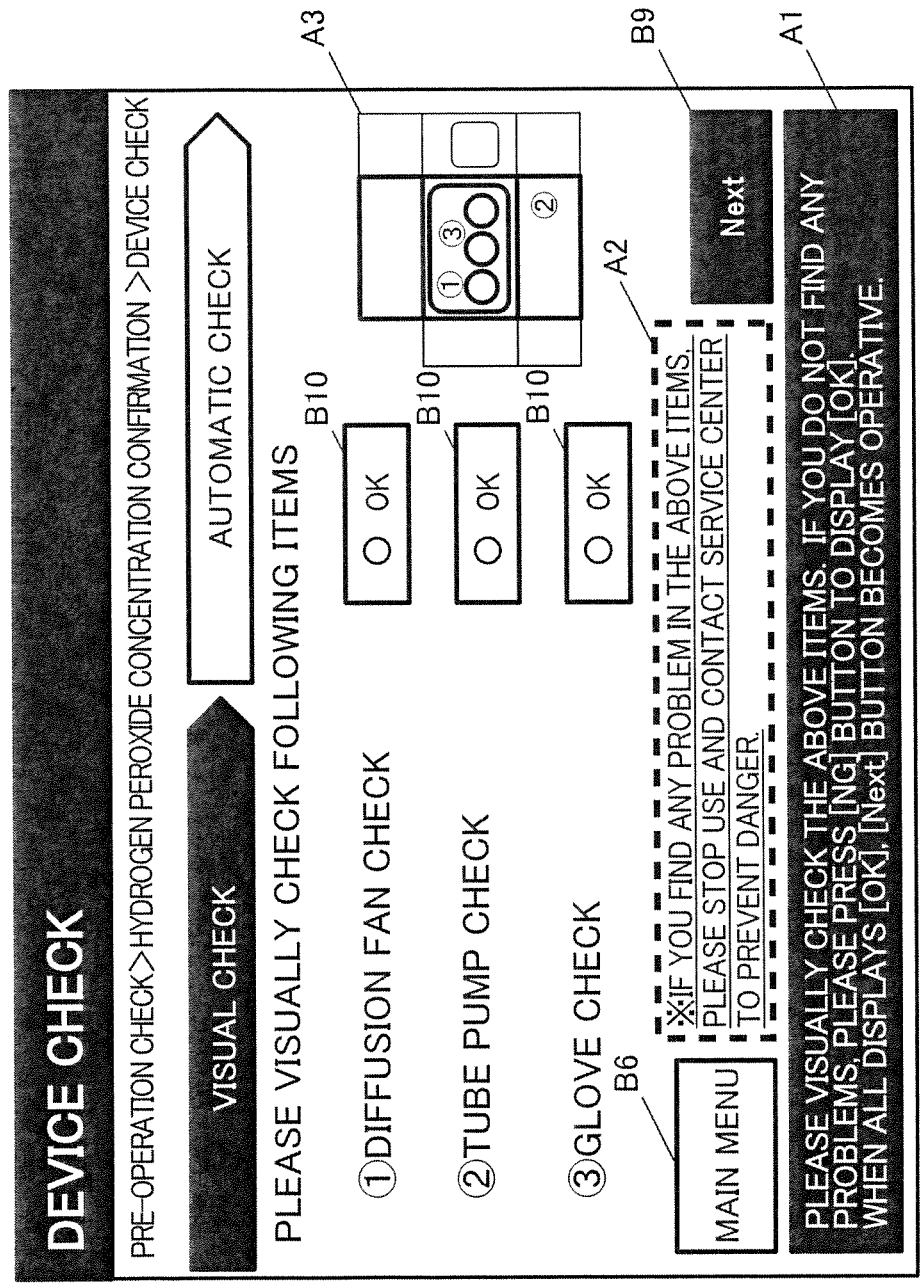
FIG. 11 is a diagram illustrating a device check screen when a visual check in the pre-operation check of the isolator system according to the first embodiment is performed.

FIGS. 10 and 11 are diagrams illustrating a device check screen when a visual check in the pre-operation check of the isolator system according to the first embodiment is performed. As illustrated in FIG. 10, the pre-operation check includes the visual check and an automatic check, and the control unit 160 displays the visual check items, which are to be visually checked by a worker in the device, on the display 111 (S106). Next to the visual check items, confirmation buttons B10 (visual check input part), to which the worker inputs the check results of the visual check items, are displayed. The display of each of the confirmation buttons B10 is switched from "NG", indicative that check is not completed, to "OK", indicative that check is completed, in response to an input from the worker. Further, the device check screen displays a [Next] button B9 to which completion of the check of the visual check items is inputted. As illustrated in FIG. 11, the [Next] button B9 becomes operative when the display of the visual check item is switched to "OK". In the case where there are a plurality of visual check items, the [Next] button B9 becomes operative when all the plurality of the confirmation buttons B10 are switched to OK. That is, if any one of the plurality of the confirmation buttons B10 displays "NG", the worker cannot input with the [Next] button B9, and when all the confirmation buttons B10 are switched to "OK", the worker can input with the [Next] button B9. When any one of the confirmation buttons B10 displays "NG", the control unit 160 holds the screen display as it is. That is, the control unit 160 displays an abnormality screen including the confirmation button B10 displaying "NG" indicative that the visual check items have not been completely checked or abnormality exists in the visual check items (S107, S108). Thus, the control unit 160 can let the worker know that there is a possibility of abnormality in the visual check items. When the worker inputs with the [Next] button B9, the control unit 160 displays the next device check screen, illustrated in FIG. 12, on the display 111 (S107, S109). Further, the visual check screen displays an information map A3 indicating which parts in the isolator system 100 correspond to the visual check items. This improves workability.

Figure 12:
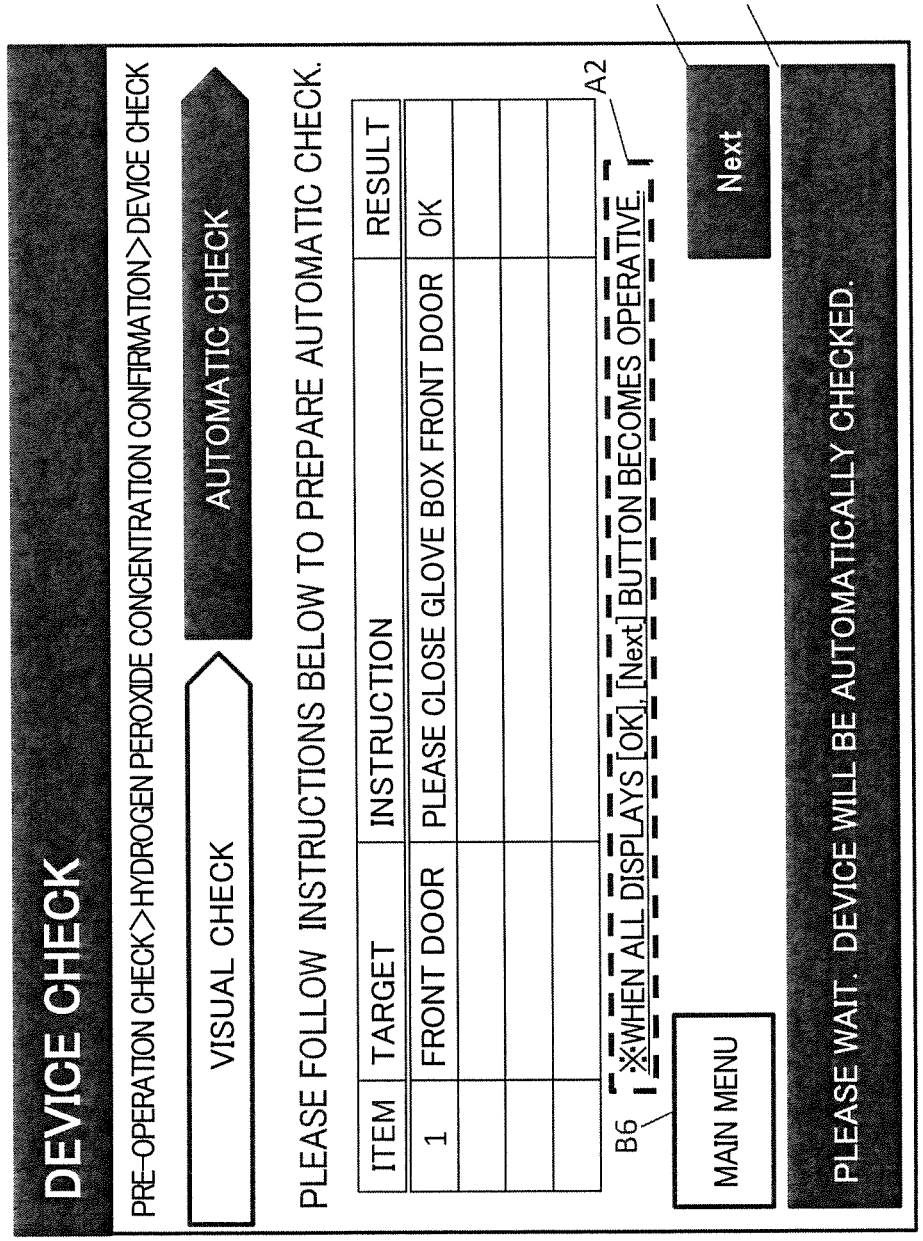
FIG. 12 is a diagram illustrating a device check screen when an automatic check in the pre-operation check of the isolator system according to the first embodiment is performed.

FIGS. 12 to 15 are diagrams illustrating the device check screens when the automatic check in the pre-operation check of the isolator system according to the first embodiment is performed. As illustrated in FIG. 12, after completion of the visual check in the pre-operation check, the control unit 160 performs the automatic check for checking items other than the visual check items. First, the control unit 160 displays guidance for a worker to confirm the predetermined items as preparation of the check, on the display 111. The control unit 160 confirms whether the predetermined items satisfy the conditions and also displays, on the same screen, whether the predetermined items satisfy the conditions. The control unit 160 displays the [Next] button B9, which becomes operative when the predetermined items satisfy all the conditions, similarly to the device check screen when the visual check is performed. When the worker inputs with the [Next] button B9, the control unit 160 displays the device check screen at the time when the automatic check is being performed, illustrated in FIG. 13, on the display 111 (S109). Further, although not illustrated in FIG. 7, in the present embodiment, when the worker inputs with the [Next] button B9, the control unit 160 locks the front door 112 as to opening/closing using the handles with locks 114.

Figure 13:
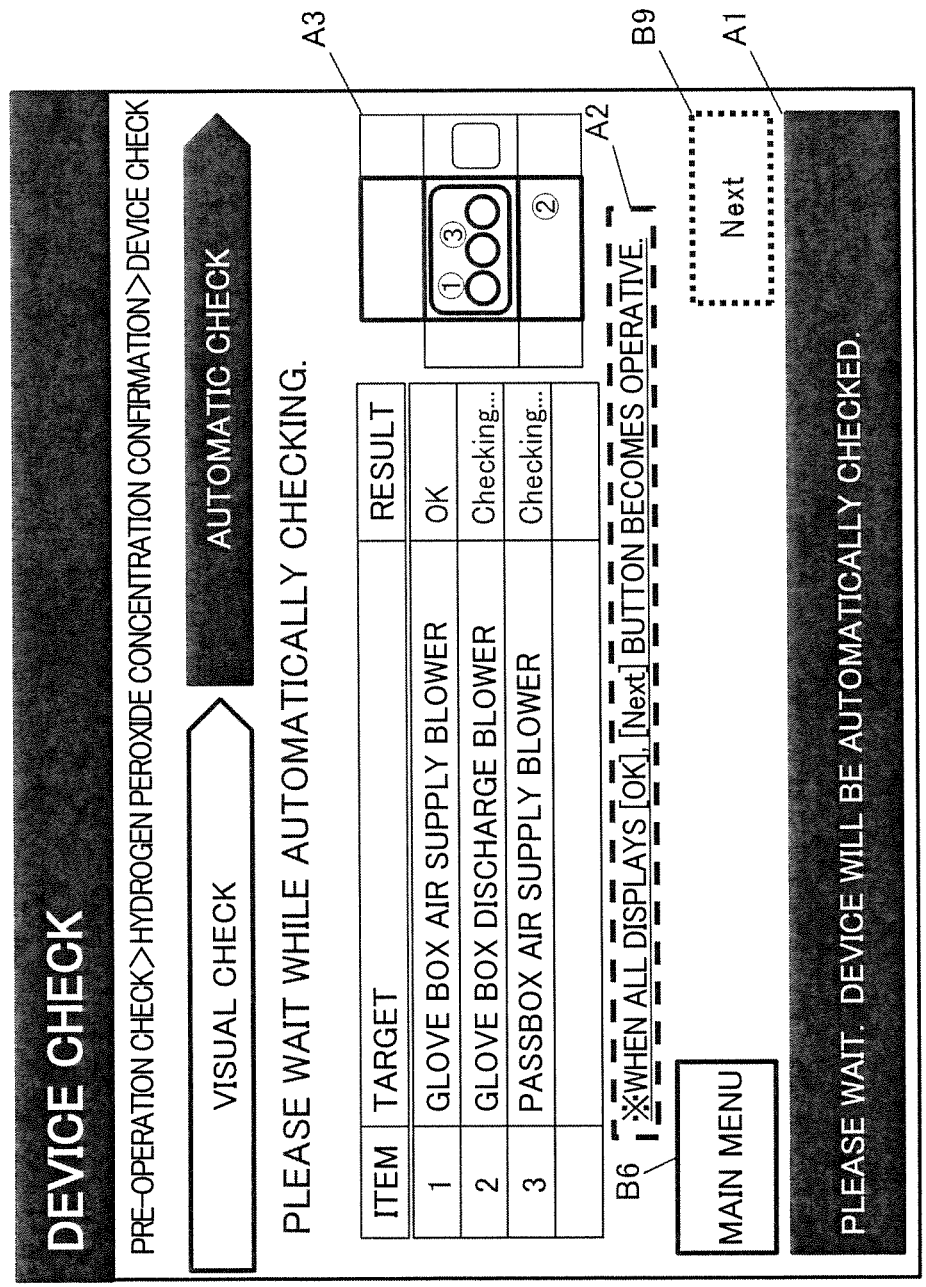
FIG. 13 is a diagram illustrating a device check screen when an automatic check in the pre-operation check of the isolator system according to the first embodiment is performed.
Figure 14:
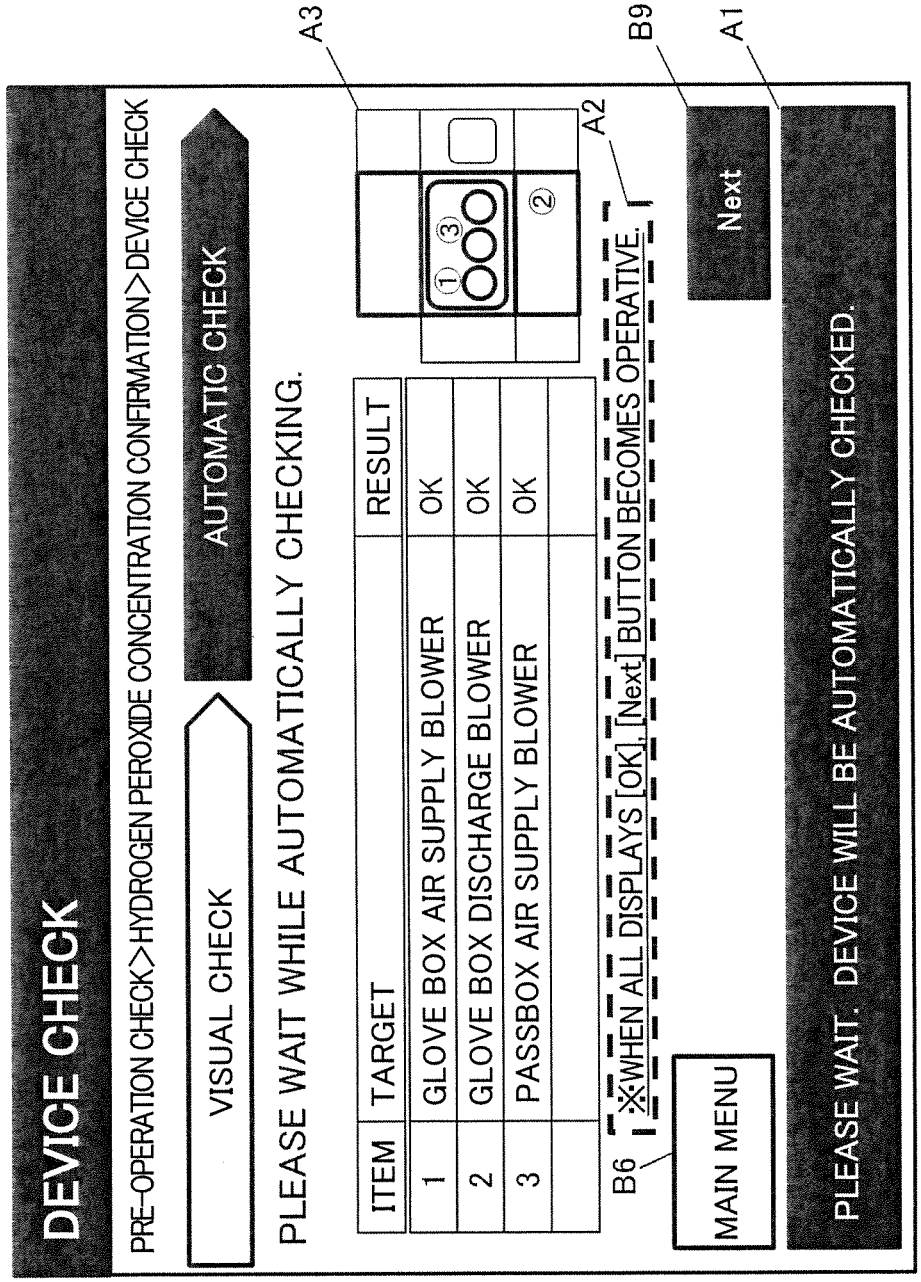
FIG. 14 is a diagram illustrating a device check screen when an automatic check in the pre-operation check of the isolator system according to the first embodiment is performed.

As illustrated in FIG. 13, the control unit 160 displays target items to be checked and the respective check results of the target items (including a display indicative of checking). As illustrated in FIG. 14, the control unit 160 displays the [Next] button B9, which becomes operative when all the items to be checked are normal, similarly to the device check screen when the visual check is performed. The control unit 160 holds the screen display as it is, if any one of the check results of the items to be checked displays "NG", on the device check screen when the automatic check is performed. That is, the control unit 160 displays an abnormality screen indicative that abnormality exists in the items to be checked (S110, S111). Thus, the control unit 160 can let a worker to know that abnormality exists in the automatic check items.

Next, when the worker inputs with the [Next] button B9, the control unit 160 confirms whether the "concentration Hi flag" is stored in the memory 162 (S112).

When the "concentration Hi flag" is stored in the memory 162, the control unit 160 transmits an operation start signal to the air conditioning unit 150, to start a detoxification process (S113). The detoxification process that is started herein is a process similar to the detoxification process performed in the sterilization process. The control unit 160 includes a counter, and measures whether a predetermined time period has passed (S114). When the predetermined time period has passed, the control unit 160 displays a screen, similar to the hydrogen-peroxide concentration confirmation screen illustrated in FIG. 8, on the display 111 (S115). When the worker selects the [YES] button B7, the control unit 160 transmits an operation stop signal to the air conditioning unit 150, to end the detoxification process (S116). On the other hand, when the worker selects the [NO] button B8, the control unit 160 starts measuring the predetermined time period again. When the predetermined time period has passed, the hydrogen-peroxide concentration confirmation screen is displayed again (S115). The control unit 160 repeats this operation until the [YES] button B7 is selected. When the detoxification process is completed (S116), the control unit 160 releases the locks of the handles with locks 114, to end the pre-operation check (S117).

On the other hand, when the "concentration Hi flag" is not stored in the memory 162, the control unit 160 releases the locks of the handles with locks 114, to end the pre-operation check (S117).

[1-3. Effects, etc.]

As described above, in the present embodiment, the isolator system 100 includes: the box-shaped glove box 110 (body case) including the work area A of a sterile environment in the interior thereof, and the at least an opening 113 (insertion portion) for a worker's arm to be inserted in the front surface thereof; the sterilizing unit 140 (sterilizing unit) configured to supply a hydrogen peroxide (sterilizing substance), to sterilize the work area A; the air conditioning unit 150 (air conditioning unit) configured to supply and/or discharge the gas with respect to the work area A; the display 111 (display unit) with which a worker can input a signal; the control unit 160 (control unit) configured to be coupled to the sterilizing unit 140, the air conditioning unit 150, and the display 111; and the memory 162 (storage unit) configured to store a signal from the control unit 160, and the control unit 160 is configured to, after startup, confirm whether the concentration of hydrogen peroxide in the work area A is equal to or less than the predetermined concentration, or not (S104 of FIG. 7), and when the concentration of hydrogen peroxide in the work area A exceeds the predetermined concentration, store in the memory 162 the "concentration Hi flag (high concentration flag)" indicative that the concentration of hydrogen peroxide in the work area A is high (S105), and thereafter, check the operation of the air conditioning unit 150 (S109), and if abnormality does not exist in the operation of the air conditioning unit 150, confirm whether the "concentration Hi flag" is stored in the memory 162 (S112), and when the "concentration Hi flag" is stored, operate the air conditioning unit 150 for the predetermined time period, to lower the concentration of hydrogen peroxide in the work area A (S113 to S116), and when the "concentration Hi flag" is not stored, end the check of the operation of the air conditioning unit 150 (S117). Here, the check of the operation of the air conditioning unit 150 includes, for example, a leakage test for confirming whether airtightness is maintained in the work area A.

Thus, the isolator system capable of improving safety for workers can be provided. For example, even in a case where the isolator system 100 is started after abnormality ends and also in such a case where the sterilizing substance remains in the glove box 110 or the like, the detoxification process can be performed by operating air conditioning unit 150 after checking the operation of the air conditioning unit 150. Therefore, such an isolator system can be provided that, even if the sterilizing substance remains in the interior at the time of startup, the device can be reliably checked, thereby being able to reduce risk of workers.

Whereas, if the detoxification process is started without performing the operation check of the air conditioning unit 150, and if airtightness in the work area A is not maintained due to a certain problem, the sterilizing substance might leak to the exterior, to expose a worker to risk. For example, damage in a glove, cracks in the front door 112 and/or a discharge pass, etc., can be considered.

Further, in the present embodiment, the control unit 160 is configured to display a concentration confirmation screen (FIG. 8) for confirming whether the concentration of hydrogen peroxide within the work area A is equal to or less than the predetermined concentration or not, and the concentration confirmation screen is configured to display a concentration confirmation input part ([YES] button B7 and [NO] button B8) with which a worker inputs whether the concentration of hydrogen peroxide in the work area A is equal to or less than the predetermined concentration, or exceeds the predetermined concentration, and the control unit 160 is configured to, when it is inputted to the concentration confirmation input part that the concentration of hydrogen peroxide in the work area A exceeds the predetermined concentration, store the "concentration Hi flag" in the memory 162 (S104, S105).

Thus, a worker can reliably measure the concentration of hydrogen peroxide within the work area A, and when the concentration is high, the worker can check the air conditioning unit 150 before the detoxification process. Therefore, such an isolator system capable of reducing risk of workers can be provided.

Further, in the present embodiment, the isolator system 100 is configured to, after startup, confirm whether abnormality existed when the previous operation ended (S101), and when abnormality existed, display warning information on the concentration confirmation screen (FIG. 8), the warning information being indicative that abnormality existed when the previous operation ended (S103), and thus, when abnormality existed at the end of the previous operation, there is high possibility of high concentration of hydrogen peroxide in the work area A, and in such a case, it is possible to draw worker's attention to risk. Therefore, safety for workers can be further improved.

Further, in the present embodiment, the control unit 160 (control system) is a control system configured to control the isolator system 100, and the control unit includes: the box-shaped glove box 110 (body case) including the work area A of a sterile environment in the interior thereof, and the at least an opening 113 (insertion portion) for a worker's arm to be inserted in the front surface thereof; the sterilizing unit 140 (sterilizing unit) configured to supply a hydrogen peroxide (sterilizing substance), to sterilize the work area A; the air conditioning unit 150 (air conditioning unit) configured to supply and/or discharge the gas with respect to the work area A; and the display 111 (display unit) with which a worker can input a signal, and the control system is configured to be couple d to the sterilizing unit 140, the air conditioning unit 150, the display 111, and the memory 162 (storage unit), and the control system is further configured to, after startup, confirm whether the concentration of a hydrogen peroxide in the work area is equal to or less than a predetermined concentration, or not, and when the concentration of the hydrogen peroxide in the work area exceeds the predetermined concentration, store in the memory 162 the "concentration Hi flag (high concentration flag)" indicative that the concentration of the hydrogen peroxide in the work area A is high, and thereafter, check the operation of the air conditioning unit 150, and if there is no problem with the operation of the air conditioning unit 150, confirm whether the "concentration Hi flag" is stored in the memory 162, and when the "concentration Hi flag" is stored, operate the air conditioning unit 150 for the predetermined time period, to lower the concentration of the hydrogen peroxide in the work area A, and when the "concentration Hi flag" is not stored, end the check of the operation of the air conditioning unit 150.

Thus, the isolator system capable of improving safety for workers can be provided. For example, even in a case where the isolator system 100 is started after abnormality ends and also in such a case where the sterilizing substance remains in the glove box 110 or the like, the detoxification process can be performed such that air conditioning unit 150 is operated after the operation of the air conditioning unit 150 is checked. Therefore, such an isolator system can be provided that, even if the sterilizing substance remains in the interior at the time of startup, the device can be reliably checked, thereby being able to reduce risk of workers.

Whereas, if the detoxification process is started without the operation check of the air conditioning unit 150, and if airtightness in the work area A is not maintained due to a certain problem, the sterilizing substance might leak to the exterior, to expose a worker to risk. For example, damage in a glove, cracks in the front door 112 and/or a discharge pass, etc., can be considered.

Further, in the present embodiment, the control unit 160 is configured to display the concentration confirmation screen (FIG. 8) for confirming whether the concentration of the hydrogen peroxide in the work area A is equal to or less than the predetermined concentration, or not, the concentration confirmation screen is configured to display the concentration confirmation input part ([YES] button B7 and [NO] button B8) with which a worker inputs whether the concentration of the hydrogen peroxide in the work area A is equal to or less than the predetermined concentration, or exceeds the predetermined concentration, and the control system is configured to, when it is inputted, to the concentration confirmation input part, that the concentration of the hydrogen peroxide in the work area A exceeds the predetermined concentration, store the "concentration Hi flag" in the memory 162. (S104, S105).

Thus, a worker can reliably measure the concentration of the sterilizing substance within the work area, and when the concentration is high, the air conditioning unit 150 can be checked before the detoxification process. Therefore, the control system configured to control the isolator system capable of reducing risk of workers can be provided.

Further, in the present embodiment, the isolator system 100 is configured to, after startup, confirm whether abnormality existed when the previous operation ended (S101), and when abnormality existed, display warning information on the concentration confirmation screen (FIG. 8), the warning information being indicative that abnormality existed when the previous operation ended (S103), and thus, when abnormality existed at the end of the previous operation, there is high possibility of high concentration of the hydrogen peroxide in the work area A, and in such a case, it is possible to draw worker's attention to risk. Therefore, safety for workers can be further improved.

Second Embodiment

An isolator system 101 according to a second embodiment will hereinafter be described with reference to FIG. 15.

[2-1. Configuration]

Since the configuration of the isolator system 101 is similar to that of the isolator system 100 according to the first embodiment, the description thereof is omitted here.

[2-2. Operation]

An operation of the isolator system 101 according to the second embodiment will hereinafter be described with reference to FIG. 15. FIG. 15 is a flow chart illustrating a pre-operation check of the isolator system 101 according to the second embodiment.

Similarly to the first embodiment, when the isolator system 101 is started, a control unit 160 firstly displays a main menu screen as illustrated in FIG. 6 on the display 111. A worker selects a menu to be operated from the main menu screen, to operate the isolator system 101. The main menu screen displays the [END] button B1 for ending the operation of the isolator system 101, the [PRE-OPERATION CHECK] button B2 for checking devices, the [OPERATION MENU] button B3 for performing the sterilization process, etc., the B4 for setting various data, and the B5 for performing authentication of a worker.

Here, with respect to a pre-operation check for checking devices, a description will be given focusing on differences with the operation of the isolator system 100, as being basically similar to the isolator system 100 according to the first embodiment.

Figure 15:
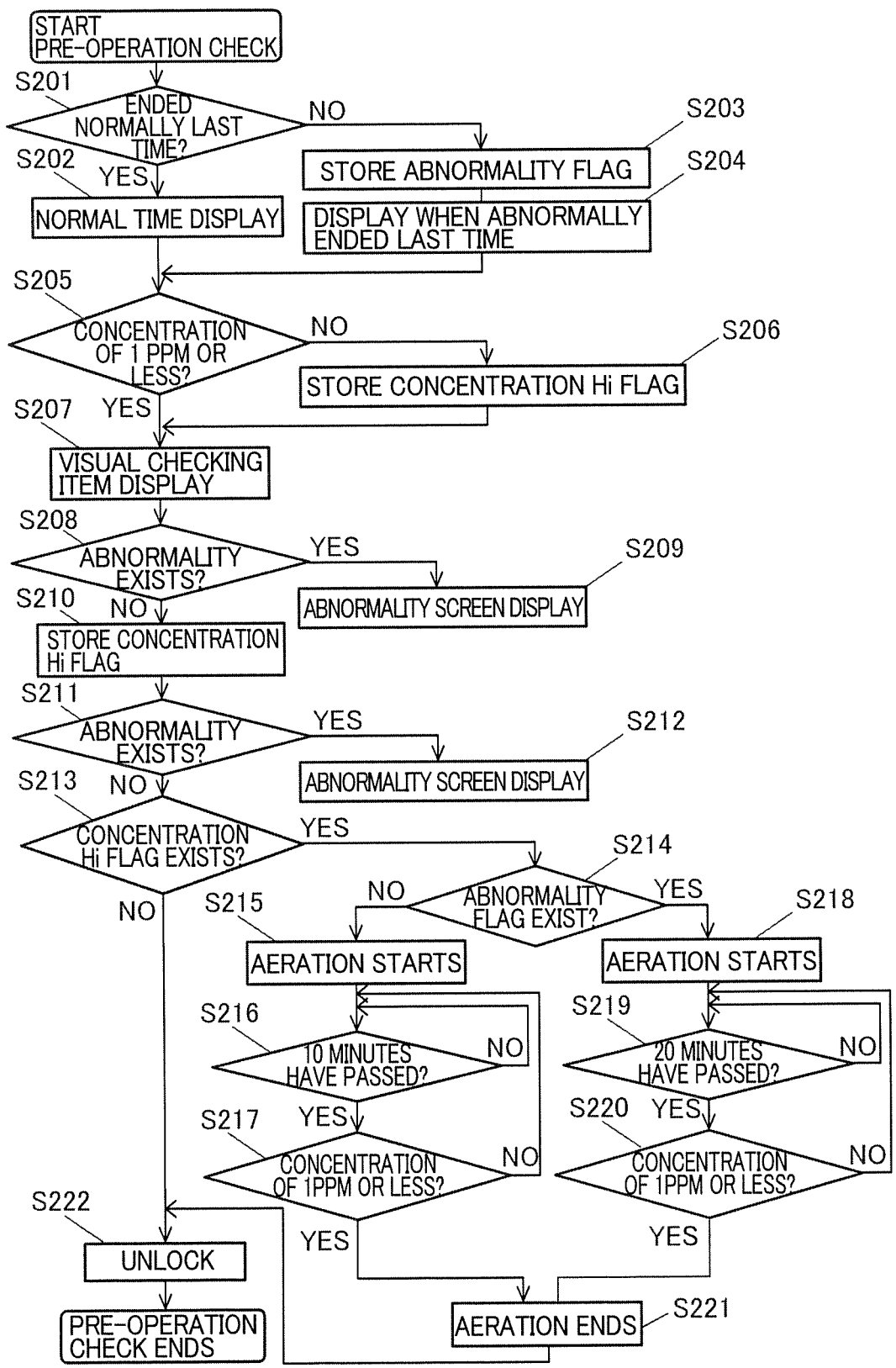
FIG. 15 is a flow chart illustrating a pre-operation check of an isolator system according to a second embodiment.

As illustrated in FIG. 15, when the pre-operation check is selected, the control unit 160, firstly, confirms whether the operation normally ended when the previous operation ended (S201). When the operation normally ended at the end of the previous operation, the control unit 160 displays the screen illustrated in FIG. 8 on the display 111 (S202).

On the other hand, when the previous operation did not normally end, that is, the operation abnormally ended last time, the control unit 160 stores "abnormality flag" in the memory 162, the "abnormality flag" being indicative that the end of the previous operation is abnormal, and thereafter display the screen illustrated in FIG. 9 on the display 111 (S203, S204).

In the second embodiment, the description of a subsequent device check process (S205 to S212) is omitted, as being similar to the device check process (S104 to S111) in the first embodiment.

Next, when a worker inputs with the [Next] button B9 in FIG. 14, the control unit 160 confirms whether the "concentration Hi flag" is stored in the memory 162 (S213).

When the "concentration Hi flag" is stored in the memory 162, the control unit 160 confirms whether an "abnormality flag" is stored in the memory 162 (S214). Thereafter, the control unit 160 transmits an operation start signal to the air conditioning unit 150, to operate the detoxification process (S215, S218). The control unit 160 includes a counter, and measures whether a predetermined time period has passed (S216, S219). At this time, the control unit 160 sets the predetermined time period in the case where the "abnormality flag" is stored in the memory 162, to a time period longer than the predetermined time period in the case where the "abnormality flag" is not stored in the memory 162. When the predetermined time period has passed, the control unit 160 displays, on the display 111, a screen similar to the hydrogen-peroxide concentration confirmation screen illustrated in FIG. 8 (S217, S220). When a worker selects the [YES] button B7, the control unit 160 transmits an operation stop signal to the air conditioning unit 150, to end the detoxification process (S221). On the other hand, when the worker selects the [NO] button B8, the control unit 160 starts measuring the predetermined time period again. When the predetermined time period has passed, the control unit 160 display the hydrogen-peroxide concentration confirmation screen again (S216, S219). The control unit 160 repeats this operation until the [YES] button B7 is selected. Here, the predetermined time period when the operation is repeated may be set shorter than the predetermined time period of the previous operation. This enables reduction in the time period of the detoxification process. When the detoxification process is completed (S221), the control unit 160 releases the locks of the handles with locks 114, to end the pre-operation check (S222).

On the other hand, when the "concentration Hi flag" is not stored in the memory 162, the control unit 160 releases the locks of the handles with locks 114, to end the pre-operation check (S222).

[2-3. Effects, etc.]

As described above, in the present embodiment, the control unit 160 is configured to, after startup, confirm whether abnormality existed when the previous operation ended, and when abnormality existed, store the "abnormality flag", indicative that abnormality existed at the end of the previous operation, in the memory 162 (S203). Then, the control unit 160 is configured to, after completion of the operation check of the air conditioning unit 150, confirm whether the "abnormality flag" is stored in the memory 162 (S214), and when the "abnormality flag" is stored, operate the air conditioning unit 150 for a time period longer than the predetermined time period (S219).

Accordingly, the concentration of the sterilizing substance in the work area A after abnormality ends has high possibility of high concentration of sterilizing substance, and in such a case, the control unit 160 can set the time period of the detoxification process longer. Thus, safety for workers can be further improved. Therefore, the isolator system and control system thereof that have high degree of safety can be provided.

Other Embodiments

Hereinabove, the first and the second embodiments have been described as exemplification of technologies disclosed in the present application. However, the technologies in the present disclosure are not limited thereto, and can be applied to embodiments to which modification, replacement, addition, omission and/or the like is made as necessary. Further, it is also possible to provide new embodiments by combining the constituent elements described in the above first and second embodiments.

Hence, other embodiments will be exemplified hereinafter.

In the first and the second embodiments, the glove box 110 has been described as an example of a body case. Since the glove box 110 includes targets to be visually checked by a worker, such as checking of a glove, etc., safety for workers can be improved. However, the body case is not limited to the glove box 110. For example, the technologies of the present disclosure may be used for the pass box 170. Further, in an isolator system coupled with a glove box, the technologies of the present disclosure may be used for a plurality of isolator systems. Further, the technologies of the present disclosure may be used for a safety cabinet and/or a clean bench. That is, a body case only has to be a device configuring a work area.

In the first and the second embodiments, the sterilizing unit 140 has been described as an example of a sterilizing unit. Since the sterilizing unit 140 is configured to eject a sterilizing mist in a mist form from a nozzle, the time period for the sterilization process can be reduced. However, the sterilizing unit is not limited to the sterilizing unit 140. For example, the sterilizing unit may be configured to supply sterilizing gas obtained by heating and gasifying a sterilizing substance with a heater. Further, the sterilizing unit may be configured to supply a sterilizing mist obtained by converting a sterilizing substance into a mist with an ultrasonic vibrator. Further, the sterilizing unit may be such that a sterilizing mist obtained by converting the substance is heated and gasified. That is, the sterilizing unit only has to be a device capable of supplying the sterilizing substance into a work area to sterilize the interior of a work area.

Further, the detoxification process according to the first and the second embodiments is configured to supply the air into the glove box 110 while discharging the gas in the glove box 110, to replace the gas in the glove box 110, thereby reducing the concentration of the sterilizing substance in the work area A. However, the detoxification process is not limited to this process. The process may be such that a sterilizing substance reduction means such as catalyst, etc., may be provided in a circulation pathway, through which the gas discharged from the work area A returns, and the gas in the work area A is circulated through the circulation pathway.

Since the isolator systems 100, 101 according to the first and the second embodiments do not include a concentration sensor, the configurations thereof are such that a worker carries out a measurement also using a detector tube and its measurement results are inputted, however the technologies of the present disclosure are not limited to such configurations. In a case where the isolator systems 100, 101 include a concentration sensor, it is not necessary for a worker to carry out concentration measurements and input measurement results, and thus the control unit 160 can omit the display of the hydrogen-peroxide concentration confirmation screen illustrated in FIGS. 8, 9.

In the first and the second embodiments, the air conditioning unit 150 has been described as an example of an air conditioning unit. Since the air conditioning unit 150 includes the air supply unit 150a and the discharge unit 150b, air conditioning can be effectively performed. Further, environmental conditions such as atmospheric pressure in the work area can be easily controlled. However, the air conditioning unit is not limited to the air conditioning unit 150. For example, the air conditioning unit may include only an air supply unit as in the air conditioning unit 180 of the pass box 170. Further, the air conditioning unit may include only a discharge unit. Further, other than the air supply unit and the discharge unit, the air conditioning unit may include a passage for supplying gas, may be configured to circulate the gas in the interior, and/or the like. That is, the air conditioning unit only has to be a device capable of supplying gas into a work area or discharge gas in the work area.

As described above, the embodiments have been described as exemplification of the technologies in the present disclosure. Accordingly, the accompanying drawings and the detailed description have been provided.

Hence, the constituent elements described in the accompanying drawings and the detailed description may include not only constituent elements required for solving the problems, but also constituent elements not required for solving the problems in order to exemplify the above technologies. Thus, even when those constituent elements not required are described in the accompanying drawings and the detailed description, it should not be immediately recognized that those constituent elements not required should be requirements.

Further, since the embodiments described above are to exemplify the technologies in the present disclosure, various types of modification, replacement, addition, omission and/or the like can be made in the scope of claims or in the scope equivalent thereto.

The present disclosure is applicable to an isolator system and a control system thereof configured to check a device at the time of startup. Specifically, the present disclosure is applicable to an isolator system, a control system thereof and/or the like used in laboratory work related to regenerative medicine and pharmaceutical production.

What is claimed is:

1. An isolator system comprising:
a box-shaped body case including
a work area, provided in an interior of the body case, in which work is conducted in a sterile environment, and
an insertion portion, provided in a front surface of the body case, into which a worker's arm is inserted;
a sterilizing unit configured to supply a sterilizing substance into the work area;
an air conditioning unit configured to supply and/or discharge gas with respect to the work area;
a display unit with which a worker inputs a signal;
a control unit configured to be coupled to the sterilizing unit, the air conditioning unit, and the display unit; and
a storage unit configured to store a signal from the control unit,
the control unit being configured to,
after startup, confirm whether a concentration of a sterilizing substance in the work area is equal to or less than a predetermined concentration, or not, and
when the concentration of the sterilizing substance in the work area exceeds the predetermined concentration, store in the storage unit a high concentration flag indicative that the concentration of the sterilizing substance in the work area is high, and
thereafter, check an operation of the air conditioning unit, and if there is no problem with the operation of the air conditioning unit, confirm whether the high concentration flag is stored in the storage unit, and
when the high concentration flag is stored, operate the air conditioning unit for a predetermined time period, to lower the concentration of the sterilizing substance in the work area, and
when the high concentration flag is not stored, end check of the operation of the air conditioning unit.

2. The isolator system according to claim 1, wherein
the control unit is configured to display a concentration confirmation screen for confirming whether the concentration of the sterilizing substance in the work area is equal to or less than the predetermined concentration, or not,
the concentration confirmation screen is configured to display a concentration confirmation input part with which a worker inputs whether the concentration of the sterilizing substance in the work area is equal to or less than the predetermined concentration, or exceeds the predetermined concentration, and
the control unit is configured to, when it is inputted to the concentration confirmation input part that the concentration of the sterilizing substance in the work area exceeds the predetermined concentration, store the high concentration flag in the storage unit.

3. The isolator system according to claim 1, wherein
the control unit is configured to,
after startup, confirm whether abnormality existed when a previous operation ended, and
when abnormality existed, display warning information on the concentration confirmation screen, the warning information being indicative that abnormality existed when the previous operation ended.

4. The isolator system according to claim 2, wherein
the control unit is configured to,
after startup, confirm whether abnormality existed when a previous operation ended, and
when abnormality existed, display warning information on the concentration confirmation screen, the warning information being indicative that abnormality existed when the previous operation ended.

5. The isolator system according to claim 1, wherein
the control unit is configured to,
after startup, confirm whether abnormality existed when a previous operation ended, and
when abnormality existed, store an abnormality flag in the storage unit, the abnormality flag being indicative that abnormality existed when the previous operation ended.

6. The isolator system according to claim 2, wherein
the control unit is configured to,
after startup, confirm whether abnormality existed when a previous operation ended, and
when abnormality existed, store an abnormality flag in the storage unit, the abnormality flag being indicative that abnormality existed when the previous operation ended.

7. The isolator system according to claim 5, wherein
the control unit is configured to,
after completion of check of the operation of the air conditioning unit, confirm whether the abnormality flag is stored in the storage unit, and
when the abnormality flag is stored, operate the air conditioning unit for a time period longer than the predetermined time period.

8. The isolator system according to claim 6, wherein
the control unit is configured to,
after completion of check of the operation of the air conditioning unit, confirm whether the abnormality flag is stored in the storage unit, and
when the abnormality flag is stored, operate the air conditioning unit for a time period longer than the predetermined time period.

* * * * *